(12) United States Patent
Finberg et al.

(10) Patent No.: US 6,583,110 B1
(45) Date of Patent: Jun. 24, 2003

(54) USE OF AGENTS WHICH BIND G PROTEINS FOR TREATING SEPTIC SHOCK

(76) Inventors: Robert W. Finberg, 48 Spring Rd., Canton, MA (US) 02021; Evelyn A. Kurt-Jones, 42 Stanley Rd., Belmont, MA (US) 02478; Keith R. Solomon, 17 Weld Hill St., Jamaica Plain, MA (US) 02130

(*) Notice: Subject to any disclaimer, the term of this patent is extended or adjusted under 35 U.S.C. 154(b) by 0 days.

(21) Appl. No.: 09/486,970
(22) PCT Filed: Sep. 4, 1998
(86) PCT No.: PCT/US98/18432
§ 371 (c)(1),
(2), (4) Date: May 23, 2000
(87) PCT Pub. No.: WO99/11281
PCT Pub. Date: Mar. 11, 1999

Related U.S. Application Data
(60) Provisional application No. 60/057,941, filed on Sep. 5, 1997.

(51) Int. Cl.[7] .......................... A61K 38/02; A61K 38/10
(52) U.S. Cl. ............................................. 514/2; 514/14
(58) Field of Search ......................................... 514/2, 14

(56) References Cited

U.S. PATENT DOCUMENTS

| | | | | |
|---|---|---|---|---|
| 5,198,420 A | * | 3/1993 | Donahoe et al. | 514/12 |
| 5,492,898 A | | 2/1996 | Bertics et al. | 514/47 |
| 5,556,757 A | * | 9/1996 | Alstyne et al. | 435/7.2 |
| 5,589,459 A | | 12/1996 | Porro | 514/15 |
| 5,589,568 A | | 12/1996 | Higashijima et al. | 530/324 |
| 5,627,262 A | | 5/1997 | Pereira | 530/324 |
| 5,652,211 A | | 7/1997 | Porro | 514/11 |
| 5,726,155 A | * | 3/1998 | Bokoch et al. | 514/13 |

OTHER PUBLICATIONS

Cabeza–Arvelaiz, Y. et al. "Cholera and Pertussis Exotoxins Protect Mice Against the Lethal Schwartzman Reaction and Antagonize the Effects of Lipopolysaccharide on Second Messenger Systems" *Lymphokine Research* 9(2):125–135 (1990).

Hailman, E. et al. "Lipopolysaccharide (LPS)–binding Protein Accelerates the Binding of LPS to CD14" *J. Exp. Med.* 179:269–277 (Jan. 1994).

Higashijima, T. et al. "Mastoparan, a Peptide Toxin from Wasp Venom, Mimics Receptors by Activating GTP–binding Regulatory Proteins (G Proteins)" *The Journal of Biological Chemistry* 263(14):6491–6494 (May 15, 1988).

(List continued on next page.)

*Primary Examiner*—Jeffrey E. Russel
(74) *Attorney, Agent, or Firm*—Lahive & Cockfield LLP; Amy E. Mandragouras, Esq.; DeAnn F. Smith, Esq.

(57) ABSTRACT

The present invention provides for the use of G protein binding agents for prophylactic and/or therapeutic treatment of septic shock. The present invention provides methods of using agents which bind G protein to treat a subject having or susceptible to septic shock. The present invention further pertains to compositions for treating a subject for septic shock. The composition includes an effective amount of a G protein binding agent such as mastoparan and, optionally, an antibiotic and a pharmaceutically acceptable carrier. Other aspects of the invention include packaged agents which bind G proteins for treating septic shock.

6 Claims, 9 Drawing Sheets

OTHER PUBLICATIONS

Higashijima, T. et al. "Regulation of $G_i$ and $G_o$ by Mastoparan, Regulated Amphiphilic Peptides, and Hydrophobic Amines" *The Journal of Biological Chemistry* 265(24):14176–14186 (Aug. 25, 1990).

Higashijima, T. and Ross, E.M. "Mapping of the Mastoparan–binding Site on G Proteins" *The Journal of Biological Chemistry* 266(19):12655–12661 (Jul. 5, 1991).

Kaziro, Y. et al. "Structure and Function of Signal–transducing GTP–binding Proteins" *Annu. Rev. Biochem.* 60:349–400 (1991).

Neer, E.J. "Heterotrimeric G Proteins: Organizers of Transmembrane Signals" *Cell* 80:249–257 (Jan. 27, 1995).

Proctor, R.A. et al. "Protection of Mice from Endotoxic Death by 2–methylthio–ATP" *Proc. Natl. Acad. Sci. USA* 91:6017–6020 (Jun. 1994).

Saito, K. et al. "Synthesis of a Wasp Venom Tetradecapeptide, Mastoparan, with a New Cleaving System for 4–Methoxy–2,3,6–trimethylbenzene–sulfonyl (mtr) Amino–Protecting Group" *Chem. Pharm. Bull.* 32(6):2187–2193 (1984).

Shenoy–Scaria, A.M. et al. "Palmitylation of an Amino–Terminal Cysteine Motif of Protein Tyrosine Kinases p56$^{lck}$ and p59$^{fyn}$ Mediates Interaction with Glycosyl–Phosphatidylinositol–Anchored Proteins" *Molecular and Cellular Biology* 13(10):6385–6392 (Oct. 1993).

Schumann, R.R. et al. "Structure and Function of Lipopolysaccharide Binding Protein" *Science* 249:1429–1431 (Sep. 21, 1990).

Solomon, K.R. et al. "The association between glycosylphosphatidylinositol–anchored proteins and heterotrimeric G protein α subunits in lymphocytes" *Pro. Natl. Acad. Sci. USA* 93:6053–6058 (Jun. 1996).

Solomon, K. et al. "G proteins regulate LPS mediated cytokine release" *Clinical Infectious Diseases* 25(2):370, Abstr. 83 (1997).

Štefanová, I. et al. "GPI–Anchoredc Cell–Surface Molecules Complexed to Protein Tyrosine Kinases" *Science* 254:1016–1018 (Nov. 15, 1991).

Sukumar, M. and Higashijima, T. "G Protein–bound Conformation of Mastoparan–X, a Receptor–Mimetic Peptide" *The Journal of Biological Chemistry* 267(30):21421–21424 (Oct. 25, 1992).

Sweet, M.J. and Hume, D.A. "Endotoxin signal transduction in macrophages" *Journal of Leukocyte Biology* 60:8–26 (1996).

Wurfel, M.M. et al. "Soluble CD14 Acts as a Shuttle in the Neutralization of Lipopolysaccharide (LPS) by LPS–binding Protein and Reconstituted High Density Lipoprotein" *J. Exp. Med.* 181:1743–1754 (May 1995).

Wurfel, M.M. and Wright, S.D. "Lipopolysaccharide–Binding Protein and Soluble CD14 Transfer Lipopolysaccharide to Phospholipid Bilayers" *The Journal of Immunology* 158:3925–3934 (1997).

Yu, B. et al. "Lipopolysaccharide Binding Protein and Soluble CD14 Catalyze Exchange of Phospholipids" *J. Clin. Invest.* 99(2):315–324 (Jan. 1997).

\* cited by examiner

| Mastoparan | − | − | + | − | + |
|---|---|---|---|---|---|
| LPS | − | − | − | + | + |
| Time (minutes) | 0 | 30 | 30 | 30 | 30 |
| Phospho-ATF-2 | | | | | |

Fig. 5B

USE OF AGENTS WHICH BIND G PROTEINS FOR TREATING SEPTIC SHOCK

RELATED APPLICATIONS

This application claims priority to PCT International Application PCT/US98/18432 filed on Sep. 4, 1998 which claims priority to U.S. Provisional Application 60/057,941 filed on Sep. 5, 1997, the contents of which are expressly incorporated herein by reference.

BACKGROUND OF THE INVENTION

Septic shock (also known as sepsis) causes more than 150,000 deaths annually in the United States. Sepsis is defined as a clinical disorder whose symptoms may include well defined abnormalities in body temperature, heart rate, breathing rate, white blood cell count, hypotension, organ perfusion abnormalities, and multiple organ dysfunction. There are several causes of sepsis including bacterial (either gram negative or gram positive), fungal and viral infections, as well as non-infective stimuli such as multiple trauma, severe burns, organ transplantation and pancreatitis.

Septic patients usually die as a result of poor tissue perfusion and injury followed by multiple organ failure. It is well recognized that many of the responses that occur during septic shock are initiated by bacterial endotoxin, a glycolipid antigen present on the surface of gram negative bacteria. This endotoxin (also referred to herein as lipopolysacchride or LPS) is released upon the death or multiplication of the bacteria and is known to activate monocytes/macrophages or endothelial cells causing them to produce various mediatior molecules such as toxic oxygen radicals, hydrogen peroxide, tumor neurosis factor-alpha (TNFα), and interleukin (IL-1, IL-6, and IL-8). These cellular and humoral inflammatory mediators evoke septic shock with symptoms ranging from chills and fever to circulatory failure, multiorgan failure, and death.

The impact of sepsis is particularly devastating to patients with compromised cardiac and hepatic function and to immunocompromised patients. Patients at high risk are elderly, chemotherapy patients and those requiring surgery or invasive instrumentation. The current therapy of antibiotics and hemodynamic support has not proven to be successful. An improved method for treating or preventing septic shock would be of great value.

The major LPS receptor for monocytes/macrophages is the glycosylphosphatidylinositol (GPI) anchored glycoprotein CD14. It is the interaction of LPS with the LPS receptor CD14 that initiates the cascade of signaling events that cause cytokine gene transcription. The precise mechanism through which LPS interacts with CD14 is unknown. Much of the controversy regarding the role of CD14 in LPS-induced signal transduction and cytokine production stems from the fact that CD14 is attached to the cell membrane by a glycosylphosphatidylinositol (GPI)-anchor and contains neither transmembrane nor cytoplasmic amino acid sequences. As such, CD14 cannot interact with signal transduction molecules in the same way as transmembrane receptors. Recently, it has been demonstrated that GPI-anchored proteins expressed on many cell types can physically interact with lipid-linked signal transduction molecules, but the functional consequences of these interactions remain unresolved (Stefanova et al., *Science*, 254: 1016–1018, 1991; Shenoy-Scaria et al., *Mol Cell Biol.*, 13: 6385–6392, 1993; Solomon et al., *Proc. Nat. Acad. Sci.*, 93: 6053–6058, 1996).

Although the precise mechanism through which LPS binding to CD14 leads to cell activation is not known, it has been demonstrated that this interaction is enhanced by the serum factor LPS-binding protein (LBP) (Shumann et al., *Science*, 249: 1429–1432, 1990; Hailman et al., *J. Exp. Med.*, 179: 269–277, 1994). The interaction of LPS/LBP with CD14 causes the exchange of LPS with lipids in target membranes (Wurfel et al., *J. Exp. Med.*, 181: 1743–1754, 1997; Yu et al., *J. Clin. Med.*, 99: 315–324, 1997; Wurfel et al., *J. Immunol.*, 158: 3925–3934, 1997). It has been suggested that this lipid transfer is responsible for LPS-induced signal transduction. The rate of the exchange reaction depends on the lipid composition of the target membranes, which has led to speculation that CD14 functions only to direct LPS insertion into particular membrane domains (Hailman et al., *J. Exp. Med.*, 179: 269–277, 1994; Wurfel et al., *J. Immunol.*, 158: 3925–3934, 1997). While the mechanism that leads to LPS-induced signal transduction has not been demonstrated, it is known that monocyte activation by LPS leads to the phosphorylation of p38 mitogen activated protein kinase (MAPK), and production of inflammatory cytokines (i.e., TNF-α, IL-6) (Sweet, M. J. and Hume D. A., *J. Leuk. Biol.*, 60: 8–26, 1996).

SUMMARY OF THE INVENTION

The present invention is based, at least in part, on the discovery that CD14 on monocytes/macrophages physically interacts with heterotrimeric G proteins and, in particular, that such G proteins specifically regulate LPS-induced mitogen activated protein (MAP) kinase activation and cytokine production in human monocytes/macrophages. This invention is further based on the discovery that agents which bind G proteins, such as G protein binding peptides, inhibit G protein signal transduction to thereby treat or prevent septic shock in vivo.

Accordingly, this invention provides compositions and methods for treating or preventing septic shock in a subject at risk of developing septic shock The method comprises administering an effective amount of an agent which binds G protein such that septic shock is treated or prevented in the subject. The agents which bind G protein are useful for both prophylactic and/or therapeutic treatments of septic shock.

The invention also pertains to compositions for treating or preventing septic shock in a subject which include an effective amount of an agent which binds G protein and, optionally, an antibiotic. The composition can further include a pharmaceutically acceptable carrier.

The present invention also provides methods for using agents which bind G proteins in combination with other agents and/or treatment regimens (e.g., antibiotics, intravenous fluids, cardiovascular and respiratory support) to prophylactically and/or therapeutically treat a subject for septic shock. Other aspects of the invention include packaged agents which bind G proteins and instructions for using such agents for treatment of septic shock.

BRIEF DESCRIPTION OF THE DRAWINGS

FIG. 1A shows that CD14 is associated with tyrosine phosphorylated proteins. FIG. 1B shows that CD14 is associated with various src kinases and heterotrimeric G protein α subunits.

FIG. 2 shows that mastoparan but not its inactive analogue (MAS-17) inhibits LPS-induced cytokine production.

FIG. 3A shows a dose-dependent inhibition of IL-6 and TNF-α production in human monocytes by mastoparan. FIG. 3B shows inhibition of LPS-, but not PMA-, induced cytokine production from human monocytes by mastoparan. The experiments shown are representative of 6 different assays with similar results.

FIGS. 5A and 5B depict the inhibition of phosphorylation of p38 MAP kinase in human monocytes and PMBC by mastoparan. FIG. 5B shows that mastoparan reduces LPS-induced p38 MAP kinase activity.

FIG. 6 shows specific inhibition of LPS-induced Erk kinase activation by mastoparan.

DETAILED DESCRIPTION OF THE INVENTION

Figure 1A:
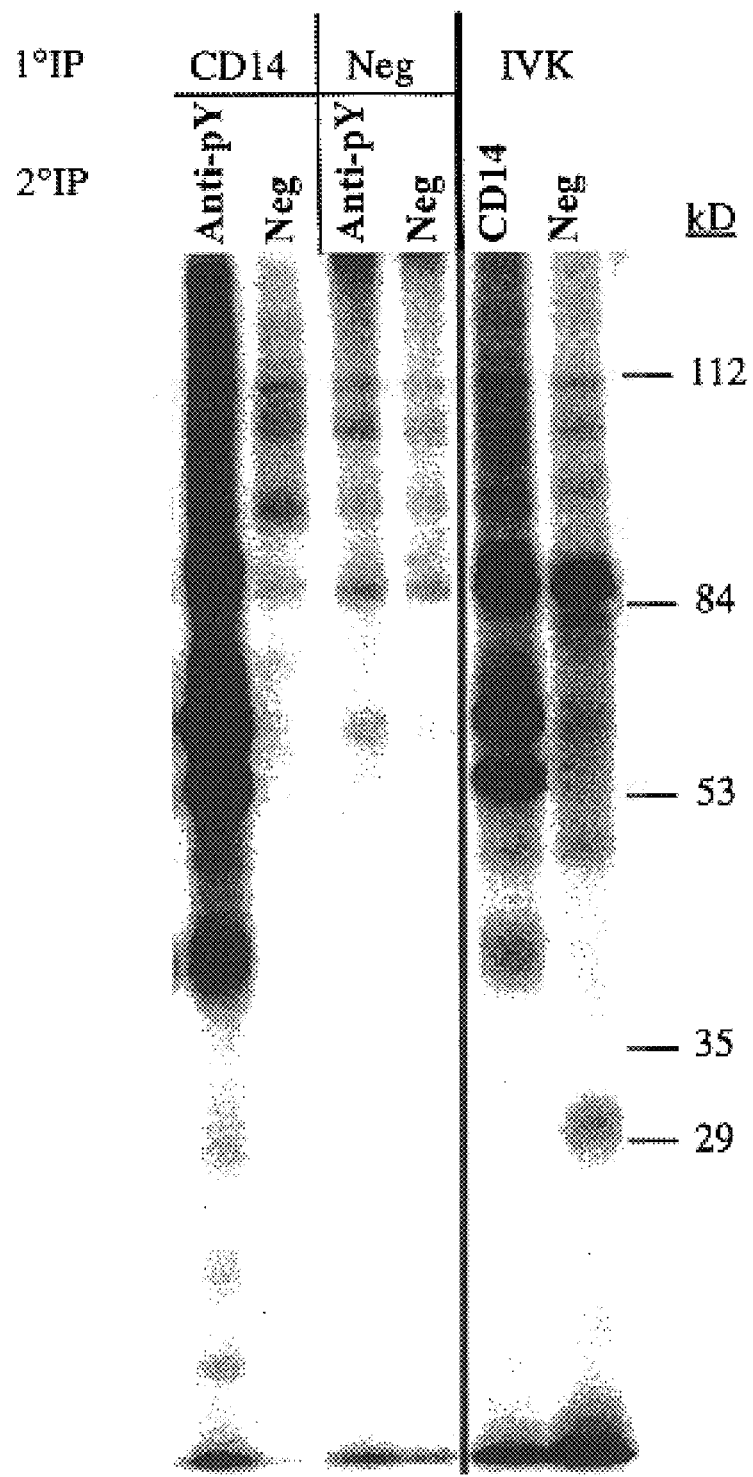
FIGS. 1A and 1B are gels depicting the association of CD14 with src kinases and heterotrimeric G proteins.

The present invention pertains to a method for treating or preventing septic shock in a subject by administering to the subject an effective amount of an agent which binds to G protein, such that septic shock in the subject is treated or prevented. Septic shock is commonly associated with bacterial infection in a surgical setting or with immunocompromised subjects, and is typically characterized by abnormalities in body temperature, heart rate, blood pressure and breathing which can progress to spontaneous clotting in blood vessels, multiple organ failure and death. The present invention also pertains to a composition for treating or preventing septic shock in a subject which includes an effective amount of an agent which binds G protein to treat or prevent septic shock in the subject. The composition can further include an antibiotic and/or a pharmaceutically acceptable carrier.

The term "septic shock" or "sepsis" refers to a clinical disorder whose symptoms may include well defined abnormalities in body temperature, heart rate, breathing rate, white blood cell count, hypertension, organ perfusion abnormalities, and multiple organ dysfunction. It may be caused by bacterial (either gram negative or gram positive), fungal, viral or other infection, as well as by non-infective stimuli such as multiple traurna, severe burns, organ transplantation and pancreatitis. Septic shock is commonly caused by "gram-negative" endotoxin-producing aerobic rods—*Escherichia coli, Klebsiella pneumoniae*, Proteus species, *Pseudomonas aeruginosa* and Salmonella. Septic shock involved with gram negative bacteria is referred to as "endotoxic shock". A significant portion of the peripheral responses occurring during septic shock are initiated by endotoxin (also referred to herein as lipopolysaccharide or "LPS"), an outer-membrane component of gram-negative bacteria which is released upon the death or multiplication of the bacteria. The manner in which LPS evokes its effects is by binding to cells such as monocytes/macrophages or endothelial cells and triggering them to produce various mediators, such as oxygen radicals, hydrogen peroxide, tumor necrosis factor-alpha (TNF-α), and various interleukins (IL-1, IL-6, and IL-8). Gram-positive bacteria, particularly pneumococcal or streptococcal, may produce a similar clinical syndrome as endotoxic shock. Thus, as used herein, the term "endotoxic shock" refers to septic shock involved with gram negative and/or gram positive bacteria.

Whatever the offending agent, the septic shock affects the peripheral circulation of a subject. The affects of septic shock include direct toxic injury to the subject which may induce arteriolar vasodilation and pooling of blood and elevated capillary pressure leading to the escape of plasma water into the interstitial compartment, further impinging on the circulating blood volume of the subject. In addition, septic shock leads to an inflammatory-immune reaction which results in the release of vasodilators in the subject, such as histamine and complement fractions, further reducing the effective circulating volume. Platelet activation and the formation of thromboxane $A_2$ may add an element of platelet aggregation, with activation of the clotting sequence and the induction of disseminated intravascular coagulation in the subject. The overall effect of septic shock in the subject is a decrease in blood volume.

The language "treat for septic shock" is intended to cover therapeutic and/or prophylactic treatments. The agents which bind G proteins can be used to protect a subject from damage on injury caused by septic shock or can therapeutically treat a subject prior to the onset of septic shock. For therapeutic treatment, agents which bind G protein can treat or reduce the damage or injury caused by septic shock in a subject having one or more symptoms of septic shock. Symptoms of septic shock in a subject include tremors, fever, falling blood pressure, rapid breathing, rapid heart beat, and skin lesions. Within hours or days, these symptoms can progress to spontaneous clotting in blood vessels, severe hypotension and multiple organ failure. The term "treat" as used herein refers reducing or preventing at least one symptom associated with sepsis. The treatment of a subject need not be complete restoration to the subjects previous state, but rather can be an amount sufficient to prevent mortality of the subject.

For prophylactic treatments, agents which bind G proteins are administered prior to the onset of symptoms of septic shock to prevent or inhibit septic shock in subjects at risk of developing or susceptible to septic shock. Subjects at risk of developing septic shock include the elderly, immunuocompromised patients (e.g., chemotherapeutic and HIV patients), patients requiring surgery or invasive instrumentation, and patients with compromised cardiac and hepatic function. Administering to a subject an agent which binds G protein in these types of settings can be used to decrease the susceptibility of these patients to septic shock.

The term "subject" is intended to include mammals having septic shock, including one or more of the symptoms related to sepsis. Examples of such subjects include humans, dogs, cats, pigs, cows, horses, rats, and mice.

The term "administering" is intended to include routes of administration which allow the agent to perform its intended function of treating or preventing septic shock by binding to G protein. Examples of routes of administration which can be used include parenteral injection (e.g., subcutaneous, intravenous, and intramuscular), intraperitoneal injection, oral, inhalation, and transderimal. The injection can be bolus injections or can be continuous infusion. Depending on the route of administration, the agent can be coated with or disposed in a selected material to protect it from natural conditions which may detrimentally affect its ability to perform its intended function. When the agent is a peptide, such as mastoparan or analog thereof, the peptide can be modified at one or more of its termini to protect the peptide from degradation. Methods of protecting peptides from degradation are disclosed in U.S. Pat. No. 5,589,568 which is incorporated herein by reference. The agent can be administered with other agents and/or with a pharmaceutically acceptable carrier. Further, the agent can be administered as a mixture of agents which bind G proteins, which also can be coadministered with a pharmaceutically acceptable carrier. The agent can be administered prior to the onset of septic shock or after the onset of septic shock.

The language "pharmaceutically acceptable carrier" is intended to include substances capable of being coadministered with the G protein binding agent, and which allows the agent to perform its intended function of treating septic shock or preventing septic shock. An example of such a carrier is saline. Any other conventional carrier suitable for use with the G protein binding agent also fall within the scope of the present invention.

The language "effective amount" of an agent which binds G protein is that amount necessary or sufficient to treat or prevent septic shock, e.g. prevent at least one of the various symptoms of septic shock, or that amount necessary to reduce the pathogenesis of septic shock. The effective amount can vary depending on such factors as the size and weight of the subject, the type of illness, the severity of the symptoms, or the particular agent used. One of ordinary skill in the art would be able to study the aforementioned factors and make the determination regarding the effective amount of G protein binding agent without undue experimentation.

The regimen of administration can affect what constitutes an effective amount. G protein binding agents can be administered to the subject either prior to or after the onset of septic shock. Further, several divided dosages, as well as staggered dosages, can be administered daily or sequentially, or the dose can be continuously infused or can be a bolus injection. Further, the dosages of the G protein binding agent(s) can be proportionally increased or decreased as indicated by the exigencies of the therapeutic or prophylactic situation.

G proteins (guanine nucleotide binding regulatory proteins) are important to regulatory mechanisms operating in all human cells. Impairment of their function can perturb the cell's response to hormonal signals and adversely affect many intracellular metabolic pathways, thus contributing to the development and maintenance of a wide variety of disease states. When functioning normally, G proteins act as an integral part of the signal transducing mechanism by which extracellular hormones and neurotransmitters convey their signals through the plasma membrane of the cell and thus elicit appropriate intracellular responses. In its simplest terms, the signal transducing mechanism of G protein can be said to comprise three distinct components. A receptor protein with an extracellular binding site specific for a given agonist; a membrane-bound effector protein that when activated catalyzes the formation of facilitates the transport of an intracellular second messenger, an example is adenylate cyclase which produces cyclic AMP (cAMP); and a third protein which functions as a communicator between these two. G proteins fulfill this vital role as communicator in the generation of intracellular responses to extracellular hormones and agonists.

G proteins are composed of three polypeptide subunits, namely G alpha ($\alpha$), G beta ($\beta$), and G gamma ($\gamma$). The conformation of each subunit and their degree of association changes during the signal transducing mechanism. These changes are associated with the hydrolysis of the nucleotide GTP to form GDP and P sub i (GTPase activity). The binding sites for GTP, GDP and the GTPase catalytic site reside in the $\alpha$ subunit.

The G protein cycle which occurs each time a signal is conveyed across the membrane can be summarized as follows: 1) in an unstimulated cell the G proteins are found in the resting state in which $\alpha$, $\beta$ and $\gamma$ are complexed together and GDP is bound to G $\alpha$, 2) the binding of an appropriate hormone or agonist to the receptor changes its conformation and causes it to activate the G protein by displacing GDP and allowing GTP to bind (this is the rate-limiting step of the G protein cycle), 4) when GTP is bound to G $\alpha$ it may dissociate from the $\beta$ and $\gamma$ complex and is able to bind to, and activate, adenylate cyclase which releases cAMP into the cytoplasm, 5) GTP is then hydrolysed to GDP and the cycle is complete.

A further attribute inherent in this system is that it allows several different receptors to interact with a signal-generating enzyme. Some act in such a way to activate the enzyme and some to inhibit it. This involves distinct alpha subunits G sub s alpha (stimulatory) and G sub i alpha (inhibitory) that combine with the same beta gamma complex to form stimulatory or inhibitory G proteins. An example of a receptor that interacts with G sub i to lower the concentration of cAMP is the alpha sub 2-adrenergic receptor. The integration of the signals from G sub s and G sub i is one of the ways in which the level of cAMP in the cell can be modulated in response to several different extracellular agonists. The present invention is based on, at least in part, the demonstration of both a physical and functional coupling of CD14 to G proteins and the involvement of G proteins in the regulation of LPS-induced signal transduction.

The term "agent which binds to G protein" or "G protein binding agent" refers to an agent which binds to G protein and inhibits G protein signal transduction, such as a small molecule, compound, drug, polypeptide, or peptide. Preferred G protein binding agents bind a G $\alpha$ subunit. Particularly preferred agents are cell permeable agents. A particularly preferred G protein binding agent for treating bacterial sepsis is a peptide. Examples of such peptides include mastoparan and analogs thereof. Mastoparan is a permeable, amphiphilic peptide that binds Gi and Go heterotrimeric G proteins (Higashijima et al., *J. Biol. Chem.*, 263: 6491–6494, 1988; Higashijima et al., *J. Biol. Chem.*, 265: 14176–14186, 1990; Higashijima et al., *J. Biol. Chem.*, 265: 14176–14186, 1991). Mastoparan is the prototype of a family of peptide toxins, collectively known as mastoparans, that form amphiphilic alpha helices. Mastoparan has been shown to stimulate guanine nucleotide exchange by G proteins in a manner similar to that of G protein-coupled receptors. The mastoparans of the present invention can be naturally occurring mastoparans, or analogs thereof, which are known in the art and are described in U.S. Pat. No. 5,589,568, incorporated herein by reference. Mastoparan can be synthesized and purified as described by Saito (*Chem. Pharm. Bull.*, 32: 2187–2193, 1984) incorporated herein by reference, or alternately can be purchased from Sigma (St. Louis, Mo.). The peptides of the present invention can be prepared by standard peptide synthesis technology (e.g., Merrifield, *J. Am. Chem. Soc.*, 88: 2149–2154, 1963; Houghton et al., *Int. J. Pept. Protein Res.*, 16: 311–320, 1980; Eler, *J. Biochem.*, 145: 157–162, 1984; *PNAS USA*, 82: 5131–5135, 1988), for example, by using a solid phase peptide synthesizer and purified by reverse phase HPLC. Such methods of peptide synthesis and purification are known in the art.

Agents which bind G proteins and inhibit G protein signal transduction can be identified by use of one or more assays known to those skilled in the art (for a review see Kaziro, Y. et al. (1991) *Ann. Rev. Biochem.*, 60: 349–400; and Neer, E. J., (1995) *Cell* 80: 249–257) or described herein. For example, G protein binding agents which inhibit G protein signal transduction can be identified by their ability to inhibit the production of cytokines (such as IL-6 and TNF- α) when cells (such as monocytes or macrophages) are contacted with the agent and a G protein stimulator, such as LPS. Alternatively, an agent which binds G protein can be identified by its ability to inhibit MAP kinase activation, under conditions as described herein. The in vivo efficacy of an agent which binds G protein and inhibits G protein signal transduction can be determined by the ability of such an agent to protect rats from LPS-induced lethal endotoxic shock as described herein.

The present invention also pertains to compositions and methods for treating a subject having septic shock or susceptible to septic shock. The composition contains an effective amount of an agent which binds G protein and a pharmaceutically acceptable treatment solution.

The present invention further pertains to the use of agents which bind G proteins together with an antibiotic for prophylactic and/or therapeutic treatments of septic shock. The invention also pertains to compositions for treating a subject for septic shock which include an effective amount of the antibiotic and an agent which binds G protein in a pharmaceutically acceptable carrier.

The present invention further pertains to the use of G protein binding agents in conjunction with other agents or regimens for therapy or prophylactic treatment of septic shock. Some specific examples of other agents or regimens which can be administered to the subject to treat septic shock include antibiotics, intravenous fluids and cardiovascular and respiratory support.

The invention is further illustrated by the following examples which in no way should be construed as being further limiting. The contents of all references, pending patent applications, published patent applications, and issued patents cited throughout this application are hereby incorporated by reference. It should be understood that the animal models used throughout the examples are accepted animal models and that the demonstration of efficacy in these animal models is predictive of efficacy in humans.

EXAMPLES

The following materials and methods were used throughout the examples.

Isolation of Human PBMC and Monocytes

Freshly isolated human peripheral blood mononuclear cells (PBMC) and monocytes were obtained from letikopaks (discarded leukocyte from platelet donations). The cells were fractionated on FICOLL-HYPAQUE™ gradients, washed, treated with tris-buffered $NH_4Cl$ to eliminate RBCs and washed to obtain PMBCs. Monocytes were obtained by depleting the PBMCs of T cells and NK cells by negative selection asking standard techniques. T cells and NK cells were removed by treatment with anti-CD3 and anti-CD2 monoclonal antibodies followed by goat anti-mouse Ig conjugated magnetic beads at a 10:1 bead:cell ratio. The monocyte preparations were at least 80–85% monocytes, as determined by anti-CD14 staining and forward and slide light scatter analysis using a FACScan (Becton-Dickenson, Elmhurst, Ill.). Less than 2% of the contaminating cells in the monocyte preparation were T cells and no NK cells could be detected. Monocytes were maintained in Ham's F-12 10% FCS, L-Glutamine and penicillin/streptomyocin at 37° C. in 5% $CO_2$.

Cell Lines

U373 cell CD14 transfectants (U373-CD14) were maintained in EMEM supplemented with 10% FCS, L-Glutamine and penicillin/streptomyocin at 37° C. in 5% $CO_2$.

Immunoprecipitation, In Vitro Kinase Assay, and Reimmunoprecipitation

Assays were performed as described in Solomon et al., Proc. Nat. Acad. Sci, 93:6053–6058 (1996). Briefly, cells were washed 3 times in cold buffered saline and were lysed on ice for 30 minutes in lysis buffer [0.5% NP40; 300 mM NaCl; 50 mM Tris pH 7.6; 0.15 u/ml aprotinin; 10 mM Iodoacetimide; 5 mM EDTA; 1 mM $Na_3VO_4$ 10 μg/ml leupeptin; 1 mM PMSF]. Insoluble debris was removed by microcentrifugation and the lysates were precleared with 100 μl (10% w/v) rabbit anti-mouse coated protein A sephrose beads (1 mg/ml) followed by 200 μl (10% w/v) protein A sephrose beads. The lysates were then incubated for two hours at 4° C. with monoclonal antibodies previously bound to protein A sephrose beads. After 2 hours, the beads were washed 4 times in lysis buffer and once in Kinase buffer [25 mM hepes, 1 mM $MnCl_2$ and 100 μM $Na_3VO_4$] and the immunoprecipitates were then resuspended in 50 μl kinase buffer with 20 μCi[$\gamma^{32}$P]ATP (New England Nuclear, Boston, Mass.) and incubated for 15 minutes at room temperature. The samples were washed 4 times in lysis buffer with 15 mM EDTA. Samples were then eluted in 0.5% SDS at 70° C. for 3 minutes or boiled in 1% SDS for 5 minutes and diluted 10 fold with cold lysis buffer. Samples were analyzed by SDS-PAGE or reimmunoprecipitated with various monoclonal or polyclonal antisera (e.g., rabbit) prior to SDS-PAGE analysis. Reimmunoprecipitated samples were boiled in reducing Laemmli sample buffer, and subjected to electrophoresis through a 10% SDS-PAGE gel.

Cytokine Production

Freshly isolated human monocytes, human PBMC and U373-CD14 cells were incubated with 10 ng/ml LPS (E coli 0111:B4, Sigma, St. Louis, Mo.), 100 ng/ml PMA or were untreated in supplemented RPMI [10% FCS; 2 mM L-glutamine and penicillin/streptomycin] with or without various concentrations of mastoparan for 18 hours at 37° C. in 24 well tissue culture dishes. IL-6 and TNF-α levels were determined by ELISA (Endogen Inc., Boston, Mass.) of supernatants harvested at 4 hours (for TNF-α) and at 18 hours (for IL-6) after LPS stimulation.

Immunoblotting

For detection of p38, phosphorylated p38 and phosphorylated Erk kinases in monocyte lysates, monocytes were subjected to various treatments and lysed in boiling reducing Laemmli sample buffer. The lysates were subjected to electrophoresis through a 10% SDS PAGE gel and were then transferred to nitrocellulose (NC). After washing twice with TBS-Twwen 20(0.1 %) the NC was placed in a solution of Ponceau S dye to ensure equal loading and left in blocking buffer [1×TBS; 0.1% TBS: 5% milk] for 1 hour. After blocking and washing, the NC was incubated with anti-p38 N+C terminus (Santa Cruz Biotechnology Inc., Santa Cruz, Calif.) for 2–3 hours or with anti-phosphorylated p38 and Erk antibodies (New England Biolabs, Inc., Beverly, Mass.) for 18 hours. Membranes were washed three times in TBS-Tween 20 and were incubated for 30 minutes with horseradish peroxidase conjugated donkey-α-rabbit antibody in blocking buffer (Amersham Corp., Arlington Heights, Ill.). Membranes were washed an additional six times [3×TBS-Tween-20; 3×TBS], and were developed by exposure to ECL chemicals (Amersham corp., Arlington Heights, Ill.) and visualized by exposure to film.

For detection of p38 in nuclear extracts, cells after a variety of treatments were subject to lysis and nuclear extraction as described in Lerder et al., *J. Immunol.* 152:77–86 (1994). The nuclear extracts were subjected to protein quantitation by Micro BCA assay (Pierce, Rockford, Ill.) using a BSA standard. The details of the blotting procedure were the same as above except that 5–10 ng of extract was used.

Lethal Endotoxin Shock

Wistar rats (200 g) were obtained from Charles River Laboratories. Rats were treated with 3 mg/kg mastoparan by intravenous injection in the tail vein, immediately followed by 15 mg/kg lead acetate and 5 µg/kg LPS 0111:B4 intravenously. Mortality was assessed up to 96 hours following LPS treatment. Mortality frequency was compared by Fisher exact test and statistical analysis was performed using Yates corrected Chi square test.

Example 1

Association of CD14 with G Proteins Following LPS Stimulation

To elucidate the mechanism of LPS-induced signal transduction mediated through CD14, CD14 was immunoprecipitated from freshly isolated human monocytes and in vitro kinase assays performed to assess the association of CD14 with phosphorylated proteins.

Figure 1B:
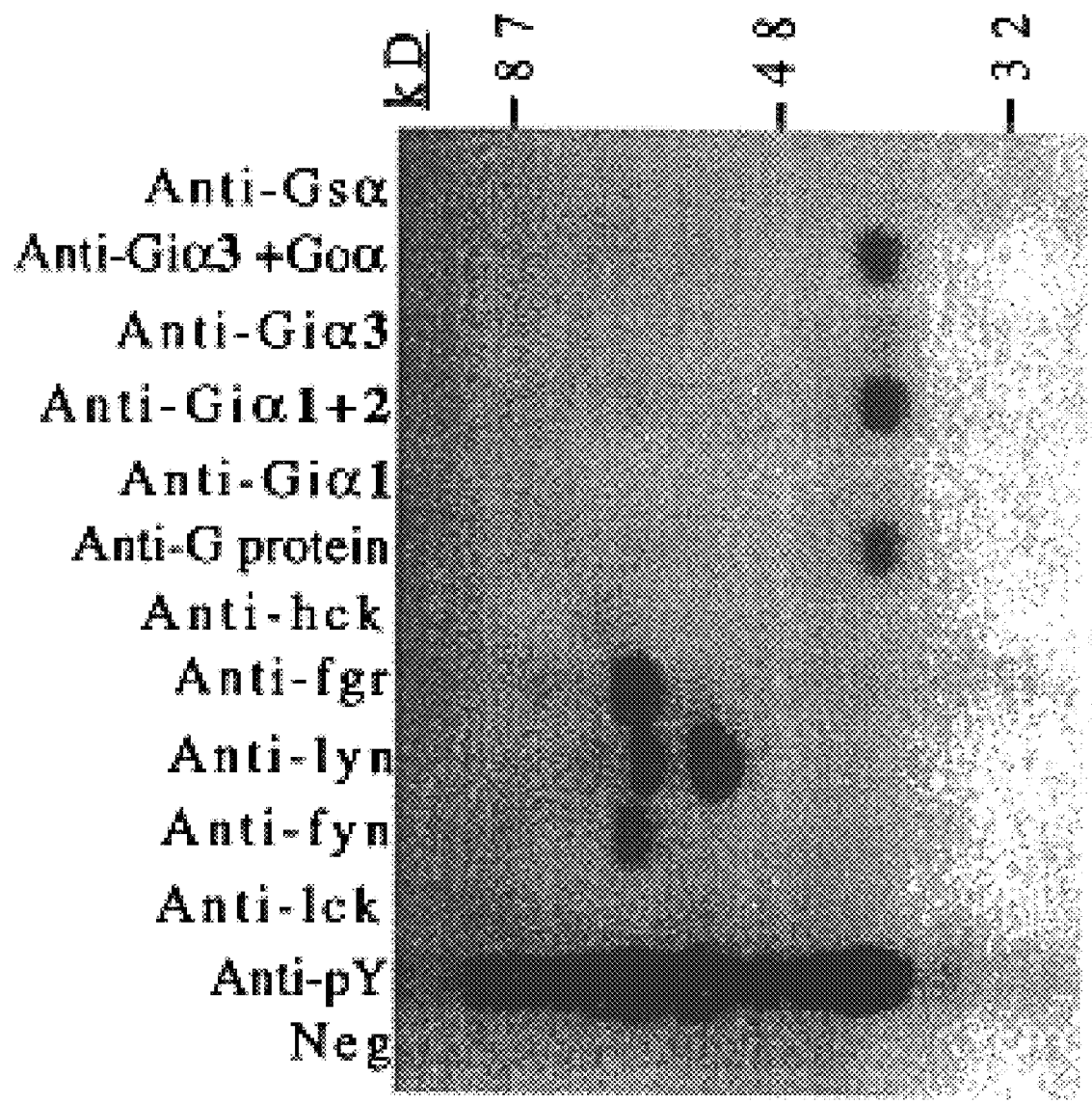

Results from these assays revealed the presence of multiple tyrosine phosphorylated species which coimmunoprecipitated with CD14 (See FIG. 1A). Reimmunoprecipitation of the product of these assays with an anti-phosphotyrosine specific antibody indicated that all the major phosphorylated species were tyrosine phosphorylated. Immunoprecipitation of the products of the in vitro kinase assay with heterosera and various monoclonal antibodies recognizing src family tyrosine kinases indicated that in human monocytes fyn, lyn and fgr src family kinases were all present in substantial quantities and a small amount of hck was observed on overexposed autoradiographs (FIG. 1B). There was no evidence for lck in the immunoprecipitates from human monocytes.

In vitro kinase assays of immunoprecipitated CD14 also revealed the presence of a 40 kD tyrosine phosphorylated species (FIGS. 1A and 1B). This protein could be immunoprecipitated from the products of CD14 in vitro kinase assays with a pan-anti-G protein antisenum which recognizes the GTP binding site of a variety of G proteins, as described in Solomon et al., *Proc. Nat. Acad Sci*, 93: 6065–6058 (1996), indicating that this species was a G protein. Immunoprecipitation of the products of the CD14 in vitro kinase assays with antisera specific for α subunits of the heterotrimeric G proteins indicated that this 40 kD protein consisted of a combination of heterometrimeric G protein α subunits of a small amount of Gi α1 and larger amounts of Gi α2, Gi α3 and Go α. In contrast, Gs α was not found in association with CD14 from the CD14 in vitro kinase assay. Similar patterns of heterometrimeric G proteins and src family kinases were found to coimmunoprecipitate with CD14 from CHO- and U373-CD14 transfectants and are similar to the patterns of phosphoproteins associated with other GPI-anchored proteins.

In addition, there was no evidence for the β or γ subunits of heterotrimeric G proteins in these immunoprecipitates. This may be due to the documented dissociation of these subunits from the α subunit during detergent lysis (Chang et al., *J. Cell Biol.*, 126: 127–138, 1994) or simply be an indication that these subunits are not phosphorylated in the in vitro kinase reactions.

Thus, the fact that CD14 immunoprecipitates contained Gi and Go heterodimer G proteins suggests that G proteins may be involved in LPS-induced signaling.

Example 2

In Vitro Effect of Mastoparan on G Protein Signal Transduction

To investigate the functional consequences of the G protein/CD14 association, human cells (i.e., monocytes and PBMCs) and U373 cell transfectants expressing CD14 were treated with mastoparan (a cell permeable, amphiphilic peptide that binds Gi and Go heterotrimeric G proteins) and LPS to determine the effect on LPS-induced cytokine production.

Figure 2:
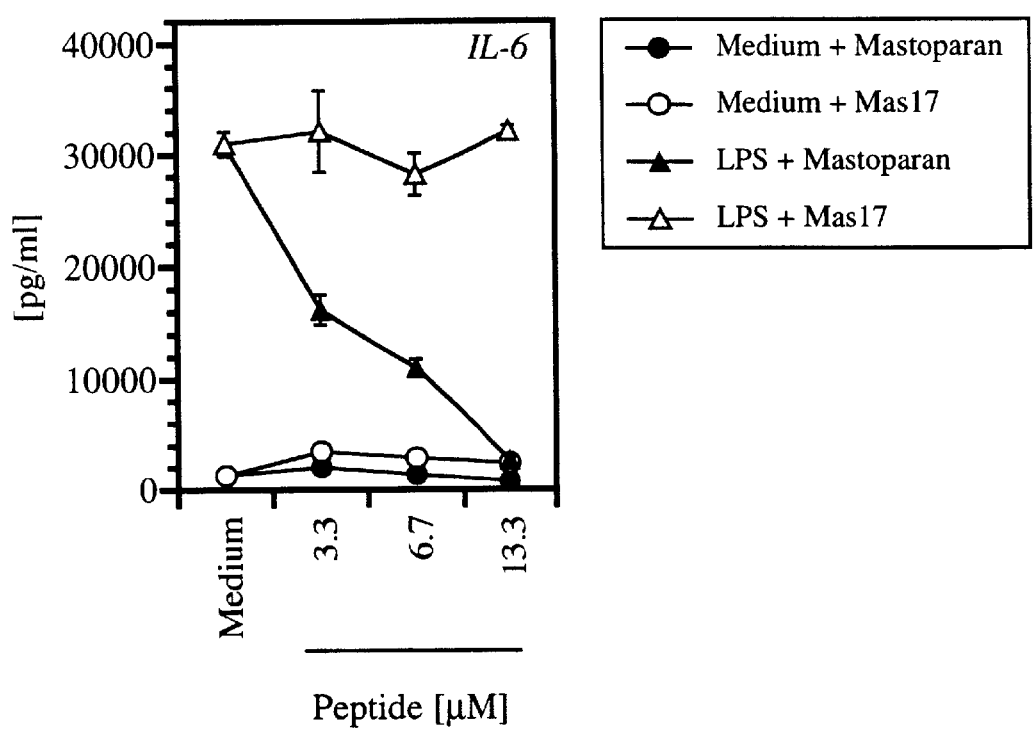
FIG. 2 depicts the inhibition of IL-6 production from LPS-stimulated PMBCs by mastoparan.

Initially, the effect of mastoparan (QCB, Hopkinton, Mass.) and its inactive analogue, MAS-17 (QBC) on cytokine production from human PBMCs were tested. Freshly isolated PBMCs were treated with LPS and/or peptides (mastoparan or the MAS-17 control peptide) and IL-6 levels were measured in the tissue culture supernatants of the cells (FIG. 2). PBMCs produced IL-6 in response to LPS, while neither mastoparan nor MAS-17 stimulated IL-6 production from the PBMCs. Mastoparan was a potent inhibitor of LPS-induced IL-6 production from the LPS stimulated PBMCs, while MAS-17 had no effect on cytokine production. The effect of mastoparan on cytokine production was dose-dependent, and at a concentration of 13.3 µM mastoparan totally ablated LPS-induced IL-6 production from the PBMCs.

Figure 3A:
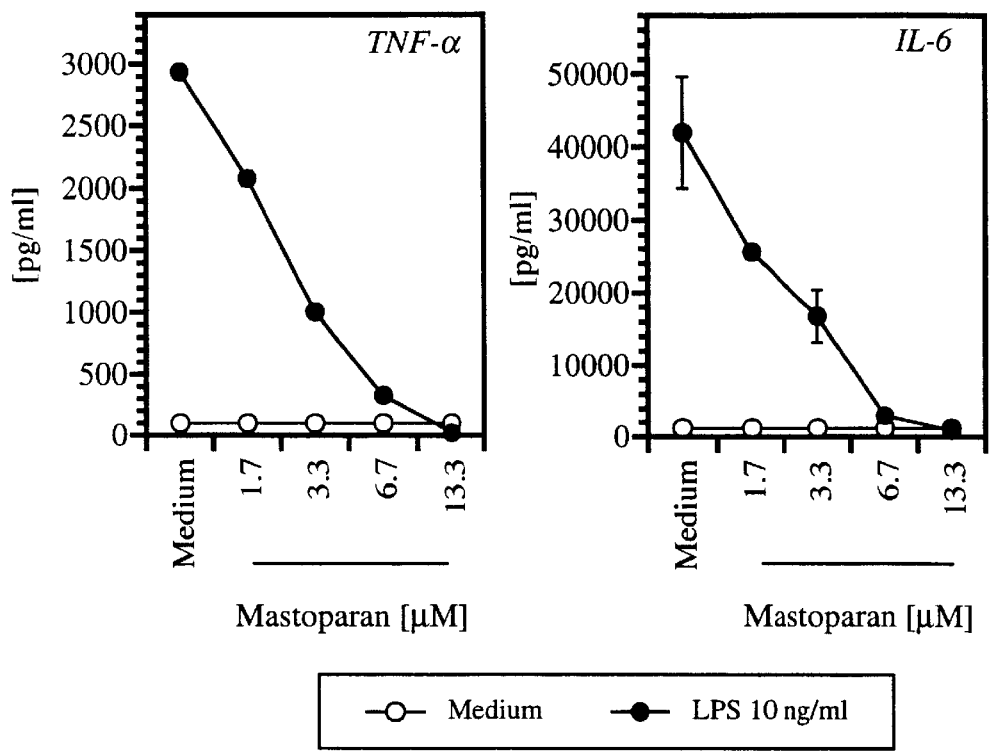
FIGS. 3A and 3B depict the inhibition of cytokine production from LPS-stimulated monocytes by mastoparan.
Figure 3B:
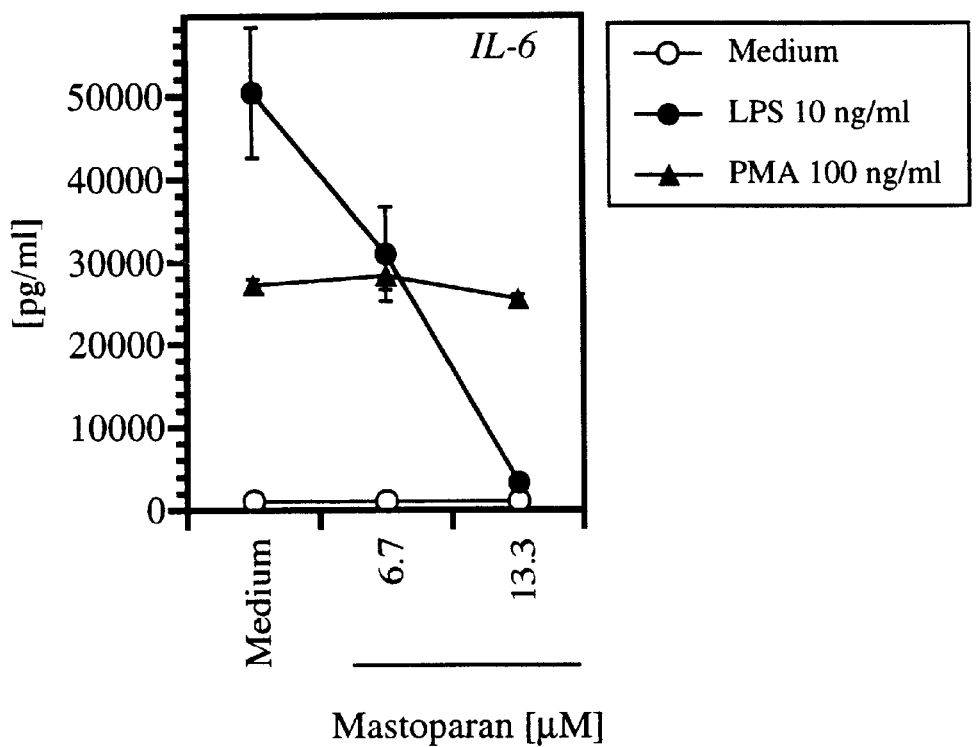

In order to determine if the effect of mastoparan on LPS-induced cytokine production was due to a direct effect on monocytes, a highly enriched monocyte population was tested for the effect of LPS and mastoparan on cytokine production from these cells. Freshly isolated human monocytes were treated with mastoparan and LPS, after which IL-6 and TFN cytokine levels were measured in the tissue culture supernatants of the cells (FIG. 3A). Untreated monocytes did not produce detectable levels of cytokines, verifying that the isolation procedure had not activated these cells. LPS caused a dose-dependent stimulation of cytokines from isolated monocytes, whereas mastoparan induced neither IL-6 nor TNF production from these cells. When mastoparan was used in conjunction with LPS, cytokine production was diminished. Concentrations of mastoparan as low as 1.67 µM caused dramatic reductions in both IL-6 and TNF production in monocytes stimulated with LPS. Mastoparan at 13.34 µM concentrations totally ablated LPS-induced cytokine production from these cells. Mastoparan had little effect on cytokine production from PMA stimulated cells (FIG. 3B), indicating the specificity of mastoparan action, and lack of mastoparan toxicity. Mastoparan had no effect on cell viability as measured by trypan blue uptake even after 36 hours of continuous mastoparan incubation.

Figure 4:
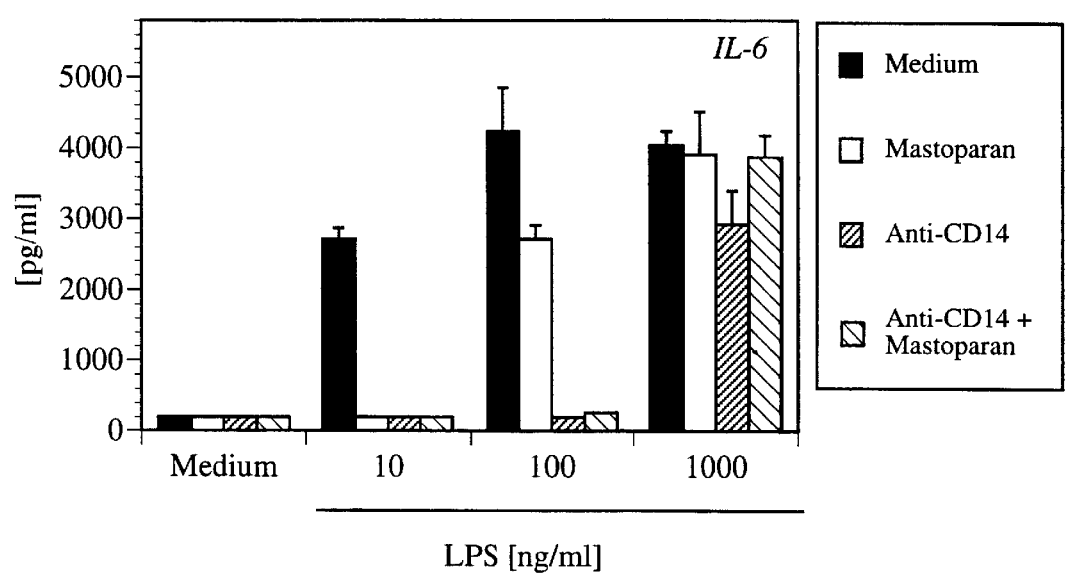
FIG. 4 shows that mastoparan only inhibits CD14-dependent LPS-induced signal transduction in U373-CD14 transfected cells.

In addition, the effect of mastoparan on LSP-induced cytokine production from an LPS responsive, CD14 transfected cell line was determined. LPS treatment of U373-CD14 transfectants induced an LPS dose-dependent production of IL-6 (FIG. 4). At low concentrations of LPS (10 ng/ml-100 ng/ml) LPS-induced IL-6 responses were completely inhibited by treatment of the U373-CD14 cells with an anti-CD14 monoclonal antibody. IL-6 production induced by 10 ng/ml LPS was also ablated by treatment of the cells with mastoparan, while at 100 ng/ml of LPS, mastoparan reduced IL-6 levels by approximately one third. At high concentrations of LPS (1 µg/ml) the IL-6 responses of these cells were not inhibited by treatment with the anti-CD14 monoclonal antibody. Thus, at high concentrations of LPS, U373 cells exhibit CD14-independent LPS induced cytokine responses. At LPS concentrations of 1 µg/ml, mastoparan was ineffective at reducing cytokine responses from these cells. Thus, CD14-independent LPS signals were not inhibited by mastoparan.

Thus, pharmacologic targeting of the same heterotrimeric G proteins which are associated with CD14 had a substantial and specific impact on LPS induction of cytokine production.

Figure 5A:
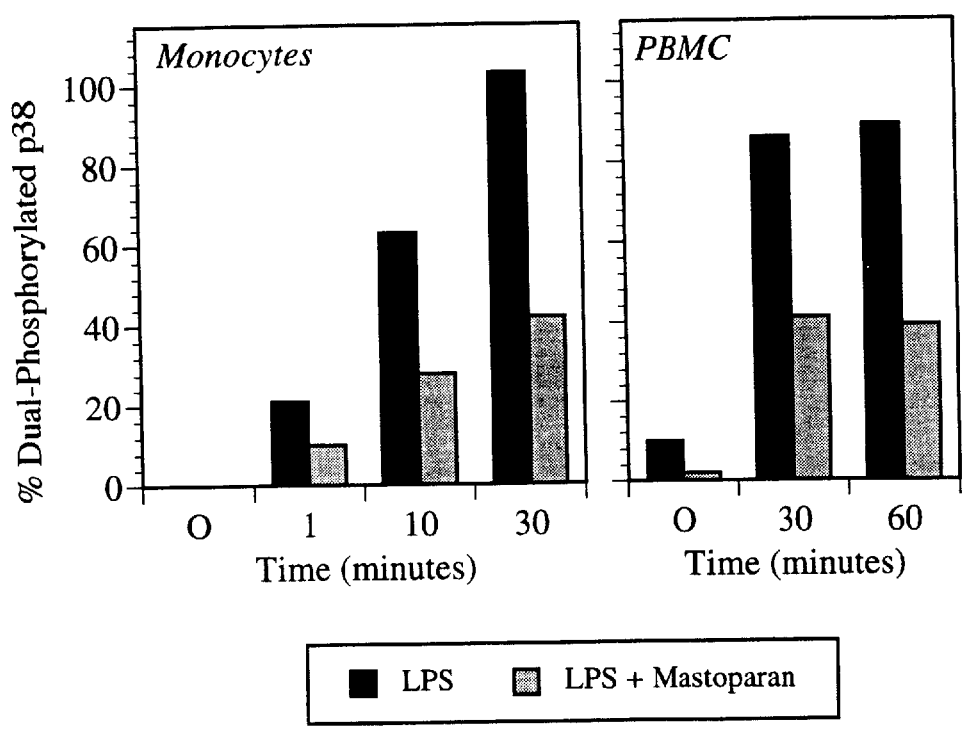

LPS stimulation of cells through CD14 leads to the induction of a MAP kinase signaling pathway involving the p38 MAP kinase, which has been shown to be specifically induced by LPS (FIGS. 5A and 5B). Because mastoparan had profound effects on cytokine production and p38 MAP kinase is involved in LPS induced-signaling, the effect of mastoparan on MAP kinase activation was evaluated. For full activation, p38 MAP kinase requires phosphorylation on both threonine and tyrosine residues (Raingeaud et al., *J. Biol. Chem.*, 270: 7420–7426, 1995). Detection of dual-phosphorylated p38 MAP kinase by monoclonal antibodies specific for the dual-phosphorylated form of p38 was used as a measure of p38 activation. Consistent with the effect of mastoparan on LPS-induced cytokine production, mastoparan reduced the LPS-induced phosphorylation of p38 MAP kinase in both monocytes and PBMC (FIG. 5A). It also inhibited LPS-induced nuclear translocation of p38.

Figure 6:
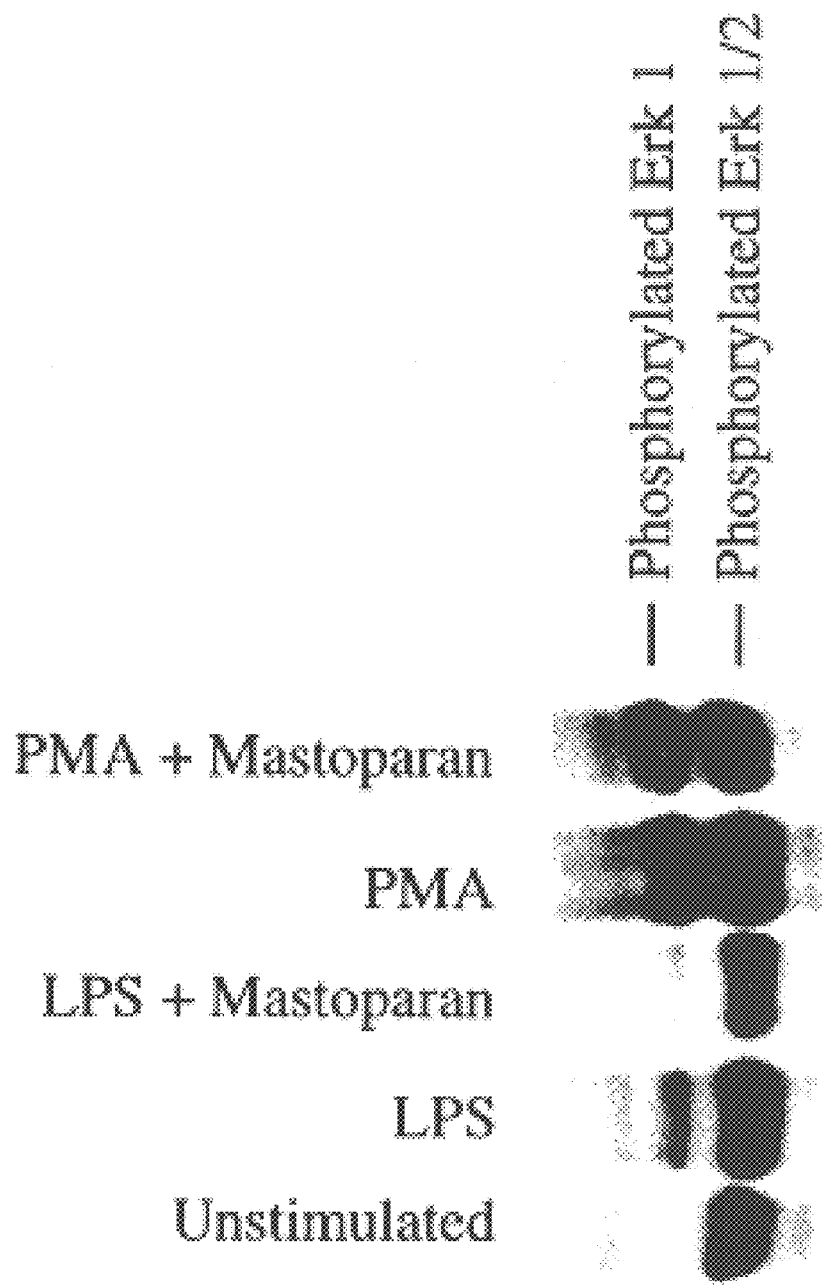
FIG. 6 is a gel depicting the effect of LPS and mastoparan on MAP kinase activation in human monocytes.

Since it had been previously demonstrated that LPS induces phosphorylation of Erk 1 and 2 MAP kinases in transformed macrophage cell lines (Weinstein et al., *J. Immunol.*, 151: 3829–3838, 1993; Weinstein et al., *J. Biol. Chem.*, 267: 14955–14962, 1992), LPS-induced activation of ERK 1 and 2 and the effect of mastoparan on the activation of these kinases in normal human monocytes was determined (FIG. 6). Only minimal phosphorylation of Erk 1 or 2 as seen in LPS-stimulated monocytes. The lack of substantial LPS-induced Erk kinase phosphorylation in freshly isolated monocytes is consistent with results obtained with other non-transformed human cells (Nick et al., *J. Immunol.*, 156: 4867–4875, 1996). In contrast to LPS, PMA induced substantial phosphorylation of Erk kinases. Interestingly, while mastoparan completely inhibited the Erk kinase activation induced by LPS, it had minimal effects on Erk kinase activation induced by PMA. This is consistent with the cytokine data, in so far as the effect of mastoparan was specific for the LPS signal transduction pathway and did not globally alter the ability to activate MAP kinases.

Example 3

In Vivo Effect of Mastoparan on G Protein Signal Transduction

The ability of mastoparan to inhibit cytokine production from human monocytes suggested that mastoparan may have efficacy in reducing LPS-induced pathology in vivo. To determine the effect of mastoparan in vivo, the effect of mastoparan on IPS-induced lethal endotoxic shock in rats was assessed.

Mastoparan did not have any toxic effects when used alone in the model system (data not shown). Mastoparan did significantly protect rats from LPS induced mortality (Table 1). These results demonstrate the importance of G protein-mediated events in endotoxic shock and that targeting heterotrimeric G proteins with pharmological agents which bind G proteins has therapeutic potential.

TABLE I

| Group | 14 hours | Mortality 24 hours | Total (%) |
| --- | --- | --- | --- |
| LPS | 14/17 | 14/17 | 82.4% |
| LPS + Mastoparan | 7/18 | 8/18 | 44.4% |

Data were subjected to Yates corrected Chi square statistical analysis. The ability of mastoparan to protect rats from LPS-induced mortality was statistically significant p<0.05 at both 14 and 24 hours. The experiment was continued for 96 hours and the mortality remain unchanged from the 24 hour point.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for treating septic shock in a subject, wherein the septic shock is endotoxic shock induced by gram positive bacteria, comprising administering to the subject an effective amount of an agent which binds G protein, to thereby inhibit the interaction of said G protein and CD14, such that septic shock in the subject is treated.

2. The method of claim 1, wherein the agent binds Gα subunit.

3. The method of claim 1, wherein the agent is a cell permeable agent.

4. The method of claim 1, wherein the agent is a peptide.

5. The method of claim 4, wherein the peptide is mastoparan.

6. The method of claim 1, further comprising administering an antibiotic to the subject.

* * * * *